United States Patent
Haberstroh

(10) Patent No.: US 6,878,947 B2
(45) Date of Patent: Apr. 12, 2005

(54) DEVICE FOR THE SIMULTANEOUS DETECTION OF RADIATION OF DIFFERENT WAVELENGTHS

(75) Inventor: Klaus Haberstroh, Bodman-Ludwigshafen (DE)

(73) Assignee: ESE Embedded System Engineering GmbH, Bodman-Ludwigshafen (DE)

( * ) Notice: Subject to any disclaimer, the term of this patent is extended or adjusted under 35 U.S.C. 154(b) by 0 days.

(21) Appl. No.: 10/666,559

(22) Filed: Sep. 22, 2003

(65) Prior Publication Data
US 2005/0023484 A1 Feb. 3, 2005

Related U.S. Application Data

(63) Continuation of application No. PCT/EP02/03182, filed on Mar. 21, 2002.

(30) Foreign Application Priority Data
Mar. 22, 2001 (DE) .......................................... 101 14 748

(51) Int. Cl.$^7$ ............................................... G01N 21/64
(52) U.S. Cl. .................................................. 250/458.1
(58) Field of Search .......................... 250/458.1, 339.01, 250/339.02, 339.05, 200; 359/634, 629, 618

(56) References Cited

U.S. PATENT DOCUMENTS

| 5,125,748 A | * | 6/1992 | Bjornson et al. | ............ 356/414 |
| 5,959,773 A | * | 9/1999 | Gagnon | ...................... 359/495 |
| 6,157,454 A | | 12/2000 | Wagner et al. | |
| 6,485,413 B1 | * | 11/2002 | Boppart et al. | ............. 600/160 |
| 2002/0125324 A1 | * | 9/2002 | Yavid et al. | ............ 235/462.45 |

FOREIGN PATENT DOCUMENTS

| DE | 3406175 | 8/1985 |
| DE | 3818278 | 2/1989 |
| EP | 0994342 | 4/2000 |
| WO | WO 94/04893 | 3/1994 |

* cited by examiner

Primary Examiner—David Porta
Assistant Examiner—Faye Polyzos
(74) Attorney, Agent, or Firm—Shlesinger, Arkwright & Garvey LLP

(57) ABSTRACT

A device for the simultaneous detection of radiation of different wavelength, comprising a number of base modules arranged one on top of the other, an optical module and an electronic module. One device each for reflecting and/or deflecting radiation of a determined wavelength-range is provided in the base modules. The light-detecting elements are associated with one of the devices each. The invention also relates to a base module, a charging unit, a method for adjusting the device and to the use of the device.

19 Claims, 6 Drawing Sheets

DEVICE FOR THE SIMULTANEOUS DETECTION OF RADIATION OF DIFFERENT WAVELENGTHS

RELATED APPLICATIONS

This application is a continuation of PCT/EP02/03182 filed Mar. 21, 2002, which claims the priority benefit of German application No. 101 14 748.1 filed on Mar. 22, 2001, both of which are hereby incorporated by reference.

The invention relates to a device for simultaneously detecting radiation of different wavelengths. Such devices are used for example to measure fluorescent dyes in the human eye. The concentrations of substances native to the body can be detected directly from the fluorescence measurements. In addition, the invention relates to a battery charging unit for a device of this kind and an opto-mechanical base module for the modular construction of a measuring device of this kind.

By detecting radiation it is possible to arrive at some conclusions regarding the concentration of the substance emitting the radiation detected.

It is known to detect or (quantitatively) determine the concentration of certain substances or compositions native to the body from the fluid in the eyes or tears. An example of this is the detection of the glucose content in the body using a fluorescence-based method. Two fluorescent substances are introduced into the human eye, for example by means of contact lenses which contain these substances. A first substance serves to measure the concentration of the native substance which is to be measured, e.g. glucose. The energy of the emitted light from the first substance depends on the concentration of the native substances in the tear fluid. The second substance serves as a reference measurement. The energy of the emitted light from the second substance is independent of the concentration of the native substance which is to be measured. The reference measurement makes it possible to eliminate fluctuations in the excitation energy and the gap between the sensor and the eye. Other examples of biochemical detection methods which may be used include luminescence, Surface Plasma Resonance (SPR), reflection, etc.

The known process was carried out or verified using standard sensors and external light sources in a laboratory environment. However, verification requires a complex experimental set-up. In order to obtain reproducible results, the measurement was carried out with constant ambient conditions.

The device used in the laboratory is unsuitable for use by a patient on a daily basis as not only is it too expensive and too large (laboratory construction) but also can only be operated under defined conditions and by trained personnel.

By contrast, a device is now proposed for simultaneously detecting radiation of different wavelengths with a number of base modules arranged one above the other, an optical module with an objective and an electronic module with light-detecting elements. In each base module is provided a device for reflecting or deflecting radiation of a predetermined wavelength range. The light-detecting elements each correspond to one of the devices, i.e. the devices deflect radiation of predetermined wavelength ranges so that this radiation strikes the corresponding light-detecting element. If, moreover, light-emitting elements are provided, these correspond to the associated devices accordingly.

The device according to the invention is preferably a hand-held device for measuring substances native to the body by optical detection in the human eye, which is so small and handy and at the same time easy to operate that it can be used by patients themselves without any specialist instructions for self-diagnosis.

However, the device according to the invention may also be used in process control, for example.

The invention is particularly suitable for use in conjunction with a fluorescence-based process as described above for measuring the concentration of glucose in the body, but is also suitable for use in measurements to determine other substances (such as lactate and other substances contained in tear fluid).

The measuring device may simultaneously reflectively measure fluorescent substances in any desired materials, such as e.g. bleaches in paper manufacture.

According to the invention, an array of three mirrors and three dichroic beam splitters or three pairs of dichroic beam splitters is provided which bring about a confocal optical path of the reference wavelength and measuring wavelength. This ensures that the measured values are not subject to changes in the angle of measurement. Moreover, the light sources used, which are advantageously light-emitting diodes, are operated in cycles, so that ambient light or scattered light can be filtered out.

The construction of the device according to the invention is modular, which means that it can be mass-produced cheaply. The basic module is preferably a board provided with bores and recesses. The bores and recesses are arranged substantially rotationally symmetrically to one another at given angular spacings. The mirrors and beam splitters are inserted in the recesses through the bores, one pair of beam splitters (two identical beam splitters) or one beam splitter and one mirror being inserted in each board. Three boards thus equipped are superimposed, for example, to form the device according to the invention, in such a way that channels for the individual optical paths are formed through the individual bores in the boards, running confocally in a section facing an objective and running separately in different channels in a section facing away from the objective. In the section facing away from the objective, either light-emitting or light-detecting elements are mounted in each channel. The mirrors and beam splitters are arranged so that a light beam emitted from a light-emitting element is reflected into a confocal optical path or the associated channel and light coming from the direction of the eye (light emitted from the substances in the eye or in the tear fluid) is reflected into an optical path or channel at the other end of which is located the associated detector element.

The excitation light sources are advantageously modulated so that the useful signal can be filtered out from the signal of the ambient light.

In fluorescence-based detection, in particular, the excitation light sources and the measuring sensors of the excitation substances used are arranged confocally in the optical path. The optical path is designed so that the distance between the excitation light sources and the eye and the distance between the sensors and the eye are identical. Thus, only one optical imaging (e.g. using an objective) is needed for all the optical paths.

The depth of focus of the imaging objective determines the sensitivity with which the measuring device behaves with regard to the distance between the measuring device and the object or eye. In a hand-held measuring device a low depth of focus is chosen, so that the distance between the eye and the measuring device has very little effect on the measuring device.

Moreover, according to the invention, a battery charger is provided for the hand-held and battery-operated device according to the invention. This charger is characterised in that data derived from the measurement and stored in a memory in the hand-held measuring device can be transferred to a receiver during a charging operation of the hand-held measuring device via a communications interface contained in the charger. The receiver may be, in particular, a data processing system in the form of a personal computer, a digital data administrator (PDA—Personal Digital Assistant) or the like.

The analogue electronics, measurement detection and storage of the measured data are advantageously integrated in the hand-held device. The current supply for these functions is preferably provided by a rechargeable battery.

The invention thus provides a hand-held measuring device which can be used as a battery-operated hand-held measuring device, i.e.
   has a compact optical structure and
   has low current consumption (battery-operated)
operates with a light energy (wavelength and intensity) which is tolerated by the eye
yields reproducible measurements which are unaffected by changes in the distance from the eye
yields reproducible measurements which are unaffected by changes in the ambient light
yields reproducible measurements which are unaffected by changes in the angle to the eye
is cheap to produce, i.e.
   is of a construction such that its assembly can be carried out automatically in large production runs and
   does not require any laborious optical adjustment
is easy to handle
has a standardised interface for storing and managing the results of the measurements.

The advantages connected with the invention are, in particular:

a. The invention makes it possible to produce a cheap hand-held measuring device for measuring substances native to the body in the tear fluid by optical detection in the human eye.
b. The invention is ideal for measuring the concentration of a defined substance native to the body.
c. The optical equipment is of modular construction from simple, mechanically identical parts.
d. There is no need to adjust the optic.
e. A separate charging/communication station serves to charge the batteries of the hand-held measuring device and at the same time acts as a communication interface between the hand-held measuring device and a standard data processing apparatus.
f. Standard interfaces are used for the communication. This can be done using a cable-bound or cable-free connection.
g. The management of the measured data can be done using standard commercial programmes.
h. The measurement is unaffected by changes in the distance between the measuring device and the eye.
i. The measurement is unaffected by changes in the angle between the measuring device and the eye.
j. Simultaneous reflective measurements of a number of fluorescent substances can be carried out in process control.

The process according to the invention for adjusting a device envisages that focussing will be carried out. This can be done, for example, by varying the distance between the device and the object which is to be measured, which is achieved by measuring the distance even while it is being changed and determining the appropriate distance or the maximum measurement by means of the pattern of the data measured, as a function of the distance.

Preferably the operation is carried out in pulses. The pulse time may be 500 ms, for example, with a total measuring time of 2 to 3 seconds. However, shorter measuring and pulse times are certainly possible.

Further advantages and embodiments of the invention will become apparent from the description and the attached drawings.

It will be understood that the features mentioned above and those yet to be described hereinafter may be used not only in the combination specified but also in other combinations or on their own, without departing from the scope of the present invention.

The invention is diagrammatically illustrated in the drawings by means of an exemplifying embodiment and will be described more fully hereinafter with reference to the drawings.

FIG. 1 diagrammatically shows a hand-held device according to the invention for measuring substances native to the body by optical detection in the human eye (hand-held measuring device) with an associated charger with a communications interface.

Figure 1:
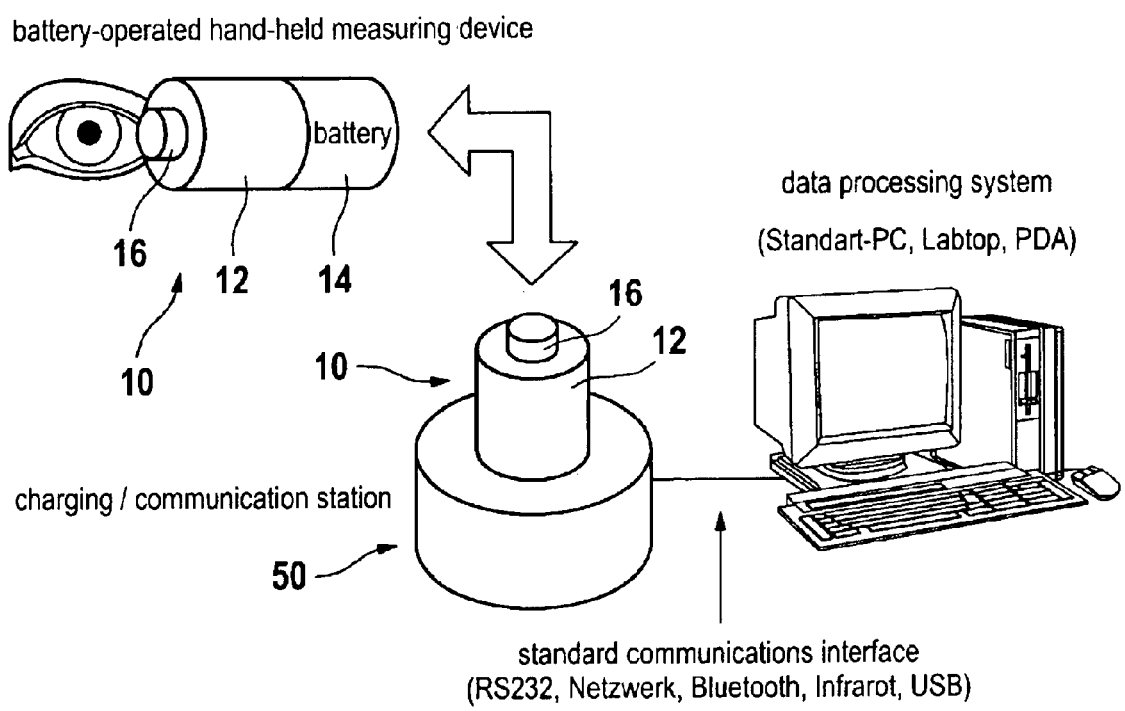

FIG. 1 shows an exemplifying embodiment of a hand-held measuring device according to the invention for measuring substances native to the body by optical detection in the human eye (hereinafter referred to as the hand-held measuring device). In FIG. 1, the hand-held measuring device 10 according to the invention which is battery-driven and by means of which light energy emitted by two fluorescent substances in the human eye can be measured is held in front of a human eye to illustrate the measuring process. The hand-held measuring device 10 is substantially cylindrical in shape. The dimensions of the hand-held measuring device 10 are such that it can be comfortably held in the hand. The excitation of the substances in order to carry out the measurement is done by means of two light-emitting elements (light sources) with a defined wavelength which are arranged inside the hand-held measuring device 10, which emerge from the hand-held measuring device through an objective 16 arranged at one end of the hand-held measuring device. If the hand-held measuring device is held in front of the eye, the light of a defined wavelength hits the eye where the substances introduced into the eye are excited. The light then emitted by the substances is guided through the objective 16 into the hand-held measuring device and detected there by means of two light-detecting elements (light-sensitive sensors). To charge the battery of the hand-held measuring device 10 it is inserted in a charger 50. The charger comprises, according to the invention, a communications interface through which data stored in a memory in the hand-held measuring device can be transferred to a data processing system during the charging process.

Figure 2:
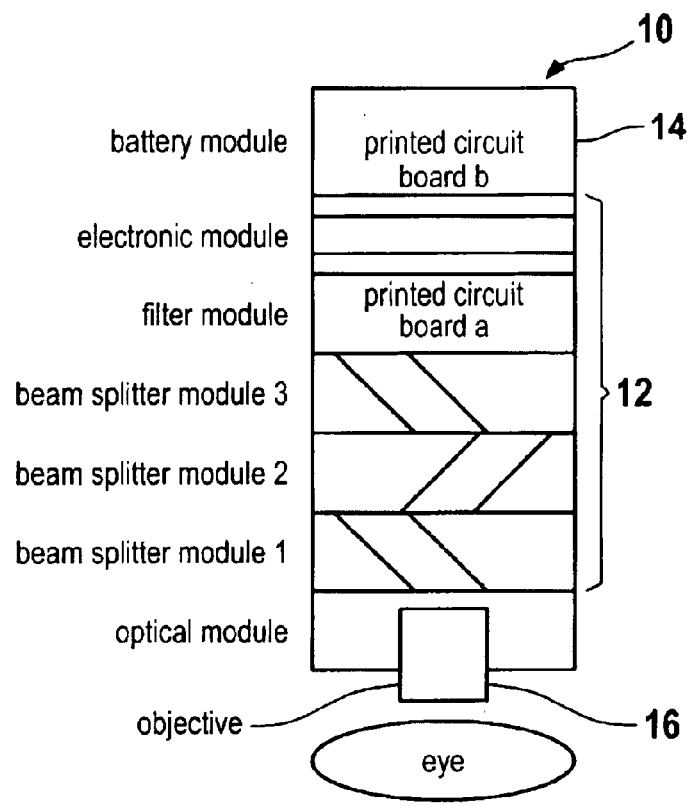
FIG. 2 shows, in highly diagrammatic longitudinal section, the structure of a hand-held measuring device according to the invention from FIG. 1.

FIG. 2 shows a highly diagrammatic longitudinal section through the hand-held measuring device 10 according to the invention to illustrate the mechanical and optical structure inside the hand-held measuring device.

The hand-held measuring device 10 comprises a central portion 12 at one end of which is mounted a battery module 14 with the battery required to operate the hand-held measuring device and at the other end of which is mounted an optical module with the objective 16. The central portion 12 of the hand-held measuring device 10 is in turn made up of a plurality of beam splitter and filter modules and an electronic module. The beam splitter and filter modules advantageously have the same structure, which is described in more detail hereinafter.

In each of the beam splitter modules 18 to 22 is mounted a dichroic beam splitter and a mirror. Another possibility is to use a pair of beam splitters which will achieve better results thanks to the prefiltering of the second beam splitter. The angle at which the mirror and beam splitter are arranged is 45°. The individual beam splitter modules are rotated through 120° relative to each other. As a result, when the beam splitter modules are superimposed, the mirrors disposed outside the central axis of the beam splitter modules are arranged in a circle around the central axis at an angular spacing of 120° in each case, when viewed from above looking down on the beam splitter modules. The dichroic beam splitters are mounted on the central axis. This arrangement results in a confocal convergence of light beams falling onto the individual mirrors and reflected back by the mirrors onto the beam splitters towards the objective, or a separation or (depending on the wavelength) passage of light falling through the objective into the hand-held measuring device by means of the arrangement of beam splitters and mirrors.

The light-emitting and detecting elements are mounted on two printed circuit boards 28 and 30 of the electronic module 26. The arrangement of the elements and the spacing of the two printed circuit boards 28, 30 are such that the optical paths for emitted and detected light are the same length as each other.

Figure 4:
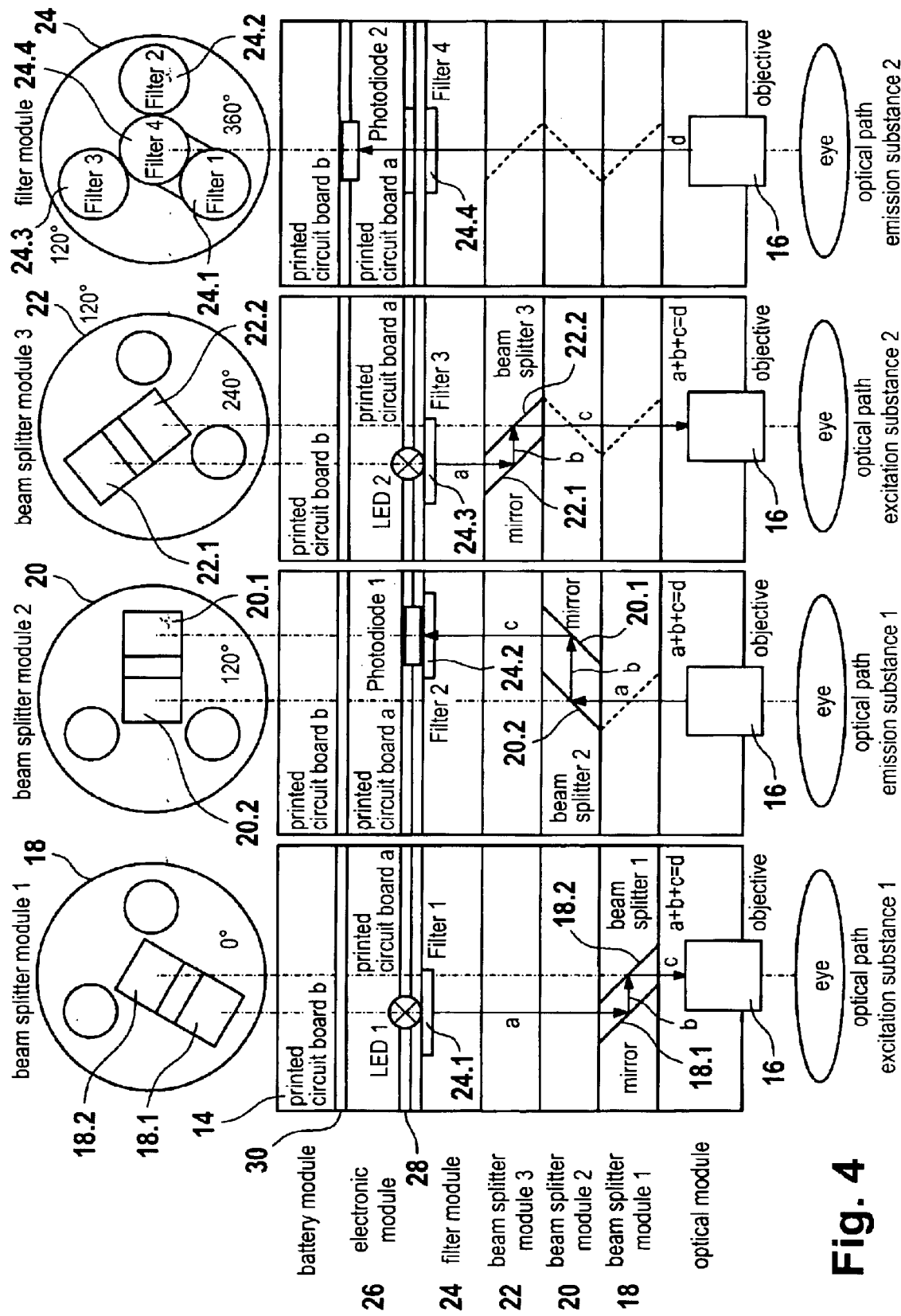
FIG. 4 shows, in highly diagrammatic longitudinal section, comparable to FIG. 2, the structure of the hand-held measuring device according to the invention from FIG. 1 with an illustration of the four optical paths and an associated cross section through the hand-held measuring device through the different modules.

As can be seen from the view in FIG. 4, a filter module 24 in which four filters are arranged is also provided on the three beam splitter modules 18, 20, 22. The filter module with the four filters is not absolutely essential, but the filters bring about a reduction in scattered light (band pass filters) which improves the quality of the measurement. Additionally or alternatively, shutters or apertures may be provided in the optical path.

Four optical paths are obtained:
Optical path 1: Light source LED 1 Eye, excitation wavelength $\lambda_{a1}$
Optical path 2: Eye Sensor Photodiode 1, emission wavelength $\lambda_{e1}$
Optical path 3: Light source LED 2 Eye, excitation wavelength $\lambda_{a2}$
Optical path 4: Eye Sensor Photodiode 2, emission wavelength $\lambda_{e2}$.

The first substance may be, for example a fluorescein with an excitation wavelength $\lambda_{a1} \cong 488$ nm and an emission wavelength $\lambda_{e1} \cong 518$ nm. The second substance is preferably rhodamine with an excitation wavelength $\lambda_{a2} \cong 560$ nm and an emission wavelength $\lambda_{e2} \cong 585$ nm.

Figure 3:
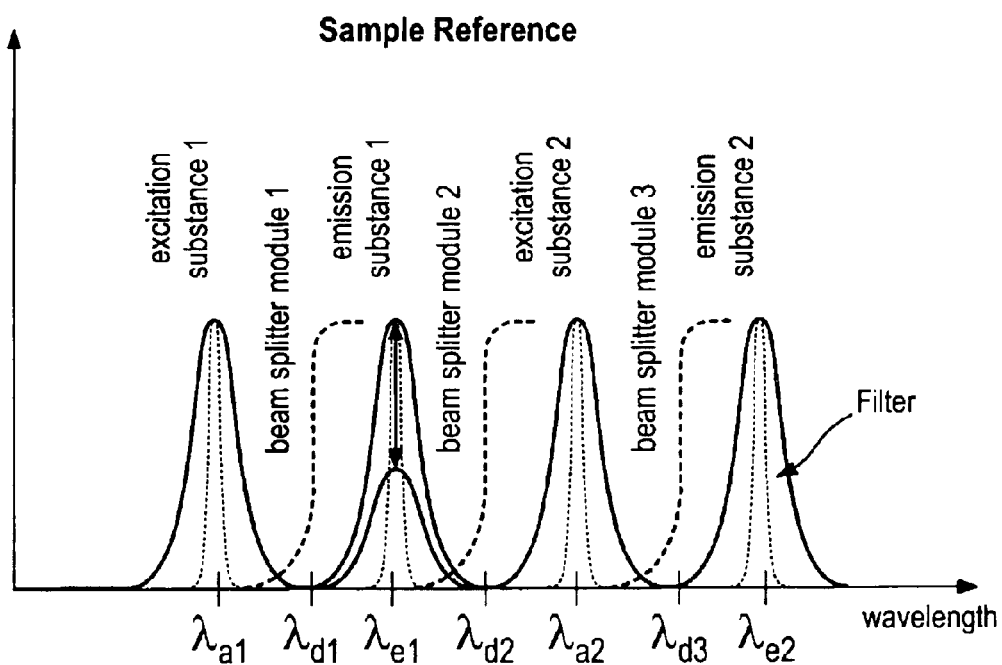
FIG. 3 shows a diagram with a spectral representation of the excitation and emission wavelengths which apply to the hand-held measuring device according to the invention from FIG. 2.

The optical construction is characterised by the following properties:
a) The four optical paths are arranged confocally. As a result, the same optical conditions of the individual optical paths are obtained relative to the angle between the measuring device and the eye.
b) The imaging of the light sources on the eye and the imaging of the emitted light on the sensor is identical for all optical paths. Thus, only one objective is needed for the imaging.
c) The separation of the individual optical paths is done by means of the dichroic beam splitters. The dichroic beam splitters have the following characteristics:
defined threshold wavelength $\lambda_d$
light with a shorter wavelength than the threshold wavelength is reflected.
light with a longer wavelength than the threshold wavelength is let through.
Three dichroic beam splitters are needed (cf. FIG. 3):
$\lambda_{a1} < \lambda_{d1} < \lambda_{e1}$
$\lambda_{e1} < \lambda_{d2} < \lambda_{a2}$
$\lambda_{a2} < \lambda_{d3} < \lambda_{e2}$.

The dichroic beam splitters are positioned at an angle of 45° to the optical path. The reflected beams are deflected again by 45° by the associated mirror, with the result that the optical path is offset parallel to the central beam. The modules with the three beam splitters and mirrors are each mounted rotated through 120° as already mentioned. Thus, the light sources and sensor of the optical paths 1 to 3 are in the same plane. No dichroic beam splitter is needed in the optical path 4. The sensor in the optical path 4 is set back by the distance from the beam splitter to the mirror for this reason. The mechanical structure for the unit of beam splitter/mirror is identical for three optical paths.

They differ only in the threshold wavelength of the beam splitters used. The optical structure with the individual optical paths is shown in FIG. 4.
d) In front of the plane of the sensors and light sources a filter module may optionally be integrated for spectrally limiting the excitation and emission energy.
e) If necessary shutters are placed in the optical path to reduce the scattered light.

Figure 5:
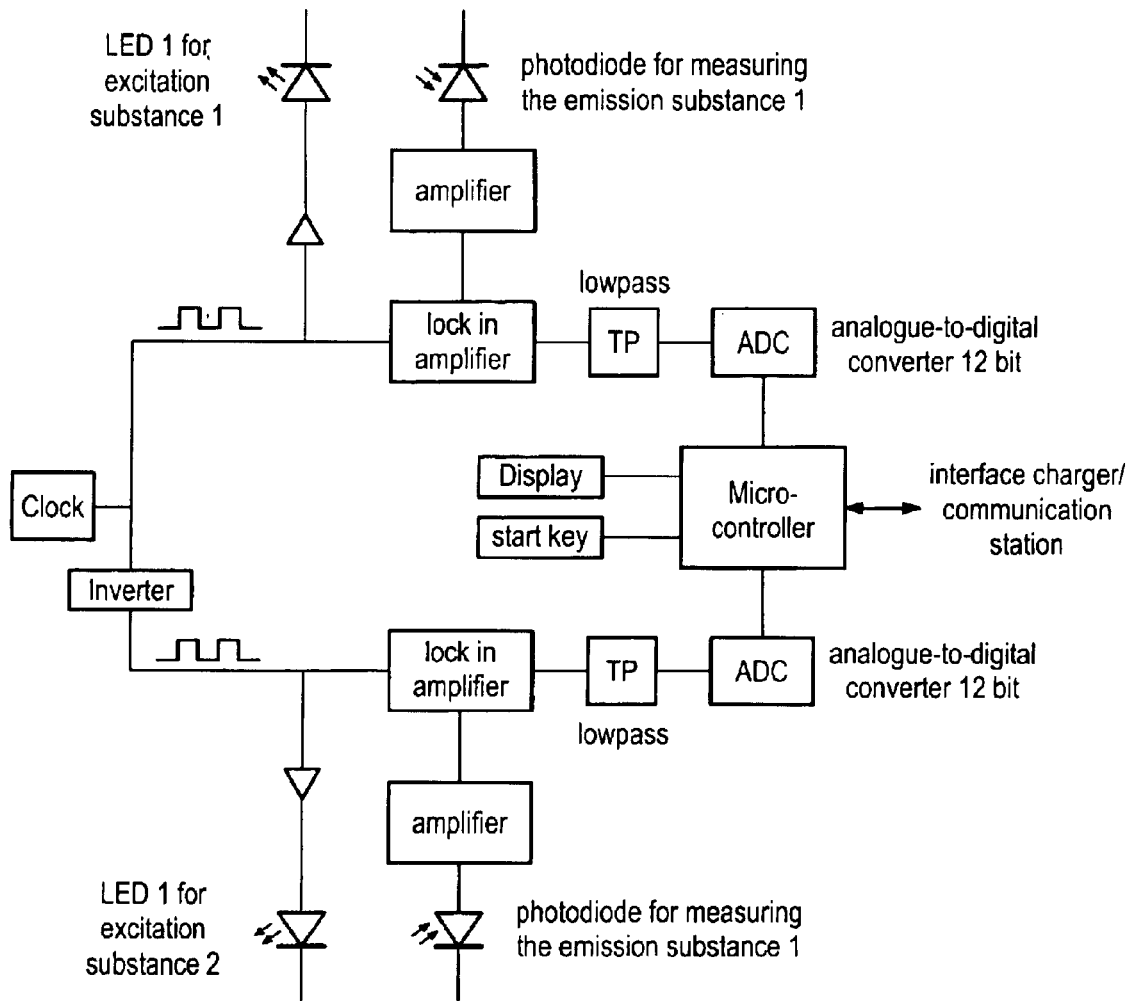
FIG. 5 shows a block circuit diagram for the electronics for actuating the light-emitting and detecting elements in the hand-held measuring device according to the invention.

In the hand-held photometer the measured data are detected, calculated and stored. It is necessary to filter out the ambient light during measurement. For this reason the light sources are actuated alternately at a defined cycle rate. The measuring signal at the sensor is amplified. The useful signal is filtered out and converted into a digital value by means of an analogue-to-digital converter (cf. FIG. 5).

The concentration of the substance to be measured is calculated from the measured value of substance 1 and the reference value from substance 2. It is not possible to obtain an absolute measurement with the measuring device according to the invention as the concentration of the fluorescent substances is not constant. The concentration of the substances to be measured in tear fluid fluctuates very considerably from one individual to another. It is therefore essential to determine the actual concentration of the substance which is to be measured, using conventional methods of investigation, and to calibrate the measuring device to these values individually. The calibrating factors are stored in the hand-held measuring device and are included in the calculation of concentration.

The measurement is started by pressing a key on the hand-held measuring device. The measured value is indicated by a display on the hand-held measuring device.

A limited number of measured data can be stored in the measuring device. The measuring device can communicate with a data processing system through a standardised interface. This may be a standard PC or a PDA (Personal Digital Assistant).

The data processing system performs the following functions:

storing the measured data for a lengthy period evaluating the measured data (statistics)

graphic representation printing reports sending the calibration data to the hand-held measuring device service/maintenance.

The communication between the hand-held measuring device and the data processing system takes place, in a particularly preferred embodiment, via a combined charger and communication station in which the batteries are charged the interface to the data processing system is established.

Advantageously, the charger has its own integrated web server so that only browser software is required on the data processing unit.

Figure 6:
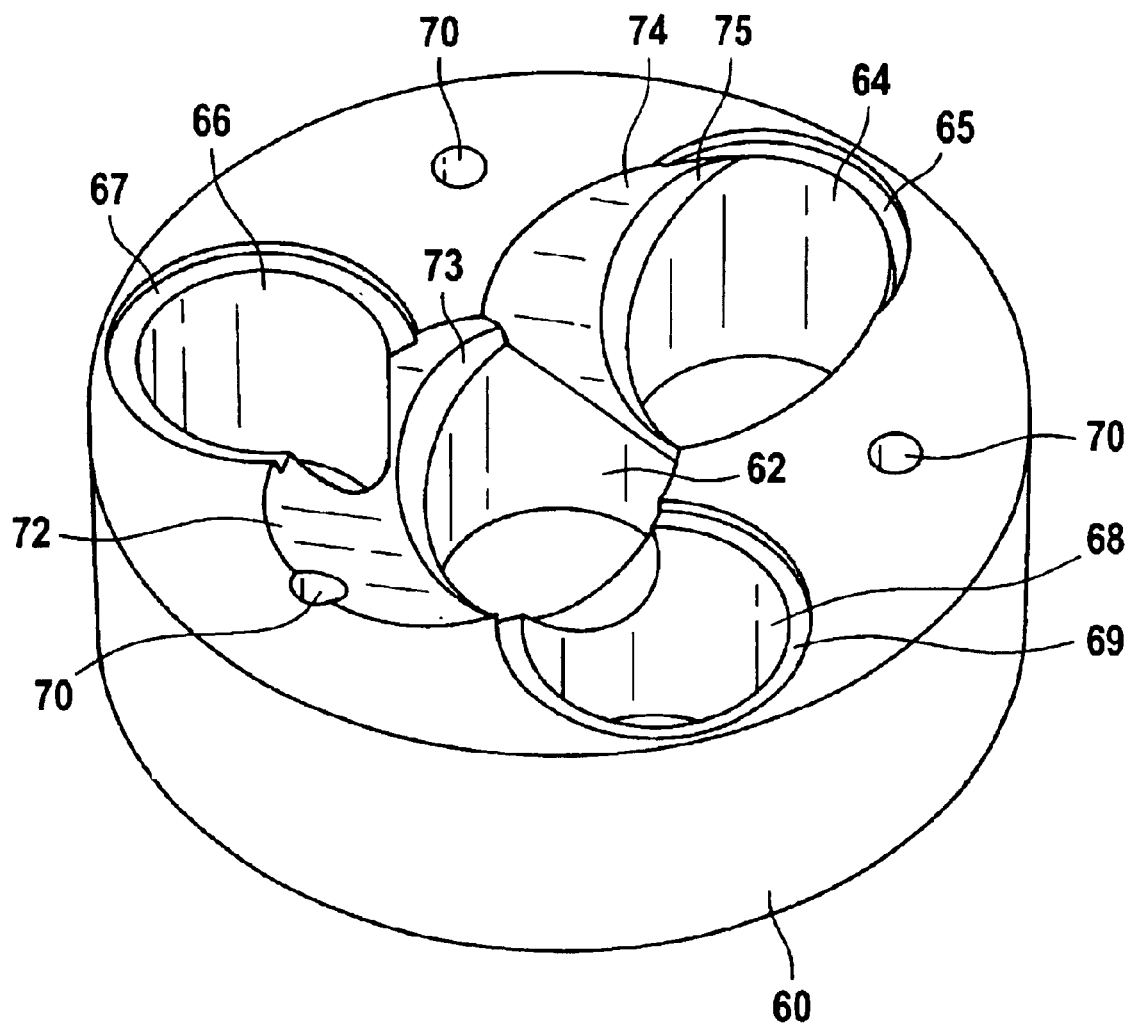
FIG. 6 is a perspective view of a board with recesses and bores forming a base module of the hand-held measuring device according to the invention.

FIG. 6 is a perspective view of a circular board 60 which serves as the base module for the construction of the hand-held measuring device according to the invention and can be used either as a beam splitter module or as a filter module.

The board 60 has a plurality of bores and recesses. A first bore 62 runs through the plate 60 coaxially with its central axis (rotation axis). Another three through-bores 64, 66, 68 are provided rotationally symmetrically around the first bore 62, equidistant from the first bore 62 and parallel thereto. The bores 62, 64, 66, 68 all have the same diameter. When a number of boards are superimposed the individual bores 62, 64, 66, 68 aligned with one another form channels which form optical path channels in the hand-held measuring device according to the invention. For equidistant and equiangular alignment, smaller pin bores 70 are provided between the three outer bores 64, 66, 68, which are at an angular spacing of 120° from one another and, when individual boards 60 are superimposed, serve to align and secure them by the insertion of pins.

Figure 7:
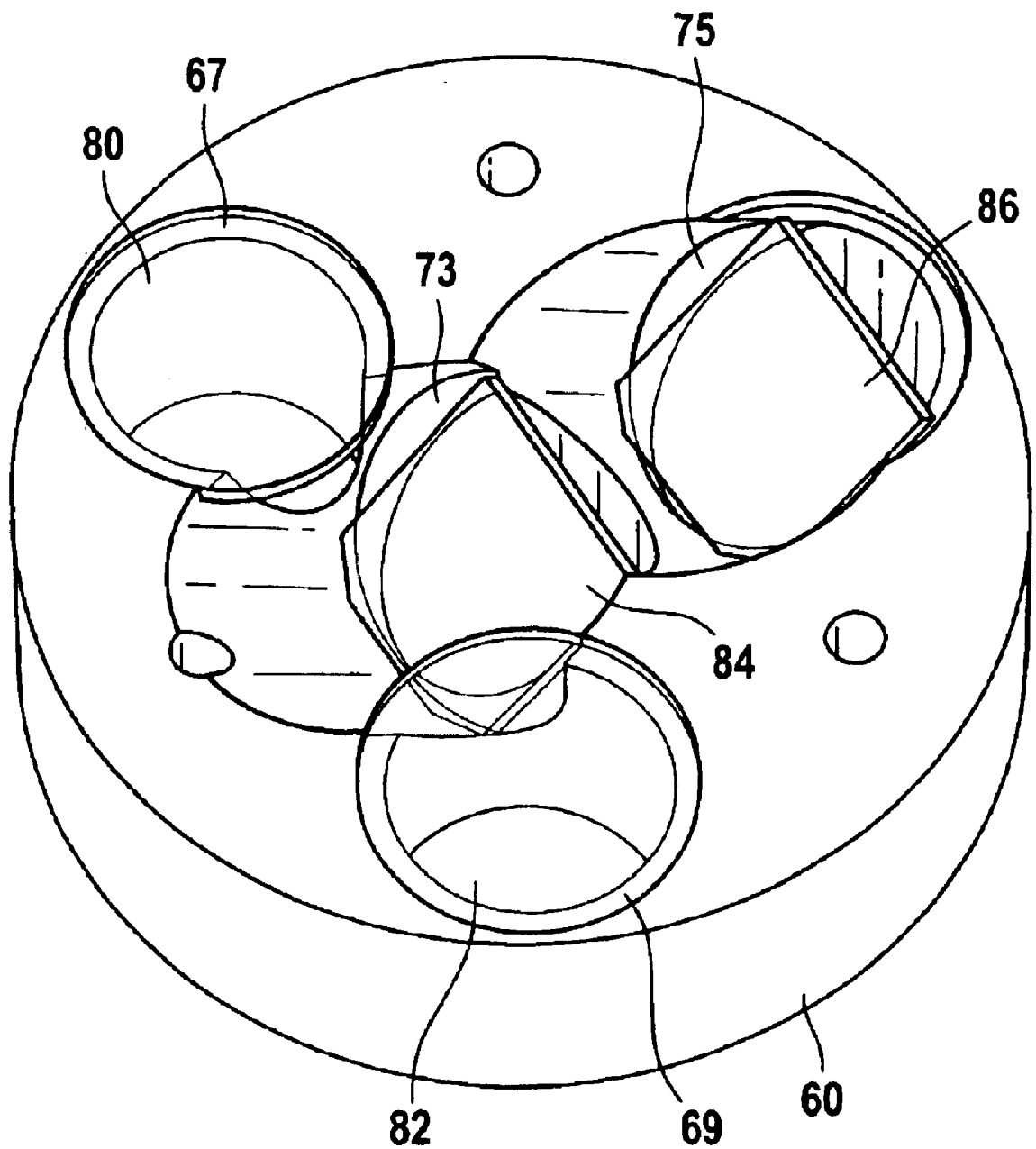
FIG. 7 shows the board of FIG. 6 with mirror, beam splitter and filters inserted.

The three peripheral bores 64, 66, 68 each have an annular shoulder recess 65, 67, 69, the diameter and height of which correspond to filter discs which are to be inserted (cf. FIG. 7, which shows a board 60 with two filter discs 80, 82 inserted).

The central bore 62 and one of the surrounding bores 64 have cylindrical recesses 72, 74 arranged at an angle of 45°, the diameter of which corresponds to the diameter of marginal dimensions of mirrors and beam splitters which are to be inserted. This diameter is greater than the diameter of the optical path bores 62, 64, so that in the region of the transition between the recesses 72, 74 and the bores 62, 64, shoulders 73, 75 are formed which have an angle of inclination of 45° and on which the mirrors or beam splitters to be used are placed (cf. again FIG. 7, in which a board 60 is shown with beam splitter 84 and mirror 86 inserted therein).

The recesses 72, 74 are constructed so that when the mirror and beam splitter are inserted a beam of light hitting the mirror perpendicularly is deflected through 90° onto the beam splitter. The optical path between the mirror and beam splitter is made possible when sufficient board material is removed between the central bore 62 and the bores 64 located underneath the mirror 86 to allow a beam to pass through.

The board 60 according to the invention which forms the base module for a hand-held measuring device according to the invention can be produced easily and cheaply by mass production by turning from a light, stable material, such as aluminium, or from a casting or injection-moulded part. To construct a hand-held measuring device according to the invention, beam splitters and mirror are inserted in three such boards and the individual boards are superimposed in a position in which they are rotated through 120° to one another and are secured against rotation by pins passed through the pin bores. If filter discs are inserted in the shoulder recesses in the individual bores, the same base module can be used as a filter module.

To summarise, a device is thus provided which is suitable in particular for measuring substances native to the body by optical detection in the human eye and which is characterised in that a) it can be produced, thanks to its compact optical structure and low current consumption, as a mobile hand-held measuring device running on batteries, b) the complete recording of measurements including calibration processes and a measured value memory is integrated in the hand-held measuring device, c) in a separate charging/communication station the batteries are charged and at the same time the measured data are transferred into a data processing system for further processing, d) it can be produced cheaply as a mass-produced item, e) no optical adjustment is needed, f) the manufacture of the modules and the final assembly of the individual modules can be automated, g) the excitation light sources are not harmful in their intensity and wavelength, h) as a result of the confocal arrangement of the optical paths the measured values are unaffected by changes in the angle of measurement, i) the measuring signal can be filtered by means of the alternating cyclical actuation of the light sources, and the measuring signal is thus largely independent of the ambient light, j) the concentration of the native substance can be calculated from a measuring signal and a reference signal and thus the distance from the measuring device and the individual properties of the eye have no effect on the measuring signal, k) calibration factors are factored into the calculation, so that the measuring device can be calibrated to the measured values of conventional absolute methods of measurement.

Moreover, a charger is provided which is characterised in that a) during the charging of the batteries of the hand-held measuring device it is possible to communicate with a data processing system through standard interfaces, b) measured data are transferred from the hand-held measuring device into a data processing system, c) parameters and calibration factors are transferred from the data processing system into the hand-held measuring device.

In one embodiment the invention relates to a measuring system for measuring the light energy emitted from fluorescent substances in the human eye. The measuring system is a measuring means in a process in which fluorescent substances are used to measure the concentration of substances native to the body in the tear fluid. The device may be constructed as a battery-operated hand-held measuring device and can be used by patients without any specialist knowledge for medical monitoring purposes. The measuring system may be produced automatically in large numbers. A separate battery charging station with integrated interface to a data processing system allows the measured data to be stored and managed.

What is claimed is:

1. Device for simultaneously detecting radiation of different wavelengths, having a number of base modules (18, 20, 22) arranged one above the other, an optical module with an objective (16) and an electronic module (26) with light-detecting elements, wherein a device (84, 86) is provided in each base module (18, 20, 22) for reflecting or deflecting radiation of a predetermined wavelength range, and the light-detecting elements each correspond to one of the devices (84, 86).

2. Device according to claim 1, wherein the base modules (18, 20, 22) are arranged rotated at a specific angle from one another to correspond to the light-detecting elements.

3. Device according to claim 1 or 2, wherein at least one light-emitting element is provided in the electronic module (26).

4. Device according to claim 3, wherein the light-emitting and light-detecting elements are arranged on printed circuit boards (28, 30).

5. Device according to one of claims 1 to 4, wherein additionally a filter module (24) is provided.

6. Device according to one of claims 1 to 5, wherein shutters are provided.

7. Charging unit for a device according to one of claims 1 to 6, with a charger and a communication module.

8. Process for adjusting a device (10) according to one of claims 1 to 6, wherein focussing is carried out in order to adjust the device (10).

9. Process according to claim 8, wherein the adjustment is made by varying the distance between the device (10) and the object which is to be measured, by measuring the distance while it is being changed and determining the appropriate distance by means of the pattern of the data measured, as a function of the distance.

10. Use of a device (10) according to one of claims 1 to 6 for measuring substances native to the body by detecting them in the human eye.

11. Base module with a first bore (62) arranged coaxially with the central axis of the base module (18, 20, 22) and a number of other bores (64, 66, 68) arranged rotationally symmetrically to the first bore (62), the first bore (62) being provided to receive a beam splitter (84) and one of the other bores (64, 66, 68) being provided to receive another reflecting element (84, 86).

12. Base module according to claim 11, wherein the additional reflecting element (84, 86) is a beam splitter (84).

13. Base module according to claim 11, wherein the additional reflecting element (84, 86) is a mirror (86).

14. Base module according to one of claims 11 to 13, wherein the beam splitter (84) and the additional reflecting element (84, 86) are arranged substantially parallel to one another.

15. Base module according to one of claims 11 to 14, wherein the central bore (62) and at least one of the other bores (64, 66, 68) have cylindrical recesses (65, 67, 69) arranged at an angle of 45°, the diameter of which corresponds to the marginal dimensions of beam splitters (84) and reflecting elements (84, 86) which are to be inserted.

16. Base module according to one of claims 11 to 15, wherein the other bores (64, 66, 68) are arranged equidistantly from one another.

17. Base module according to one of claims 11 to 16, wherein the other bores (64, 66, 68) and the central bore (62) have the same diameter.

18. Base module according to one of claims 11 to 17, which is constructed as a board (60) with a round outline.

19. Base module according to one of claims 17 to 18, wherein pin bores (70) are provided in surfaces which adjoin one another on adjacent base modules (18, 20, 22).

* * * * *